United States Patent [19]

Dixon et al.

[11] Patent Number: 5,733,768
[45] Date of Patent: Mar. 31, 1998

[54] AMYLOID PRECURSOR PROTEIN PROTEASE

[75] Inventors: Eric P. Dixon; Edward M. Johnstone; Sheila P. Little; Franklin H. Norris, all of Indianapolis, Ind.

[73] Assignee: Eli Lilly and Company, Indianapolis, Ind.

[21] Appl. No.: 361,395

[22] Filed: Dec. 22, 1994

Related U.S. Application Data

[62] Division of Ser. No. 891,542, May 28, 1992, abandoned.

[51] Int. Cl.$^6$ ........................................ C12N 9/64
[52] U.S. Cl. ................................................ 435/226
[58] Field of Search .................................. 435/226

[56] References Cited

U.S. PATENT DOCUMENTS

| | | | |
|---|---|---|---|
| 5,292,652 | 3/1994 | Dovey et al. | 435/226 |
| 5,424,205 | 6/1995 | Dovey et al. | 435/226 |

FOREIGN PATENT DOCUMENTS

| | | |
|---|---|---|
| 91/13904 | 9/1991 | WIPO. |
| 92/00374 | 1/1992 | WIPO. |
| 92/03542 | 3/1992 | WIPO. |
| WO92/07068 | 4/1992 | WIPO. |

OTHER PUBLICATIONS

Abraham Carmela R. et al., 174(2) Biochemical and Biophysical Research Communications 790(91).
Ishiura S., Journal of Neurochemistry 363(91).
Kang, J. et al., Gene 110 181(92).
Nelson, Robert B. and Siman, Robert, 265(7) The Journal of Biological Chemistry 3836(90).
Selkoe, Dennis J. 32 Scientific American 66(91).

*Primary Examiner*—Keith D. Hendricks
*Attorney, Agent, or Firm*—Paul J. Gaylo

[57] ABSTRACT

This invention provides an APP-cleaving protein and related nucleic acid compounds. The invention also provides methods, materials and assays. The compounds of this invention will further the characterization of neurological diseases such as Alzheimer's disease and Down's syndrome.

2 Claims, No Drawings

1

AMYLOID PRECURSOR PROTEIN PROTEASE

This application is a division of application Ser. No. 07/891,542, filed May 28, 1992, now abandoned.

BACKGROUND OF THE INVENTION

A peptide of 42 to 43 residues known as the β-amyloid peptide (β/A4) has been implicated in Alzheimers's disease and Down's syndrome. Researchers hypothesize that abnormal accumulation of this 4 Kd protein in the brain is due to cleavage of a larger precursor protein, called amyloid precursor protein (APP). Normal cleavage of APP occurs within the A4 region, indicating that an alternate cleavage event occurs when the normal full length is generated. The amino terminal residue of β/A4 is often an aspartic acid (Asp), indicating that a protease which cleaves between the methionine (Met) at position 596 ($Met_{596}$ using the numbering system according to Kang J. et al., 325 Nature 733 (1987).) and $ASP_{597}$ of APP would generate amyloid. Therefore, proteases which cleave the APP so as to generate β/A4 are important tools for characterizing Alzheimer's disease and Down's syndrome.

In the past, researchers have attempted to characterize the abnormal cleavage event through the use of classical protein purification techniques. These investigations have resulted in reports of a partially purified 68 kilodalton (Kd) protease which cleaves at a Met-Asp bond of a synthetic peptide. Abraham C. et al., 11A Neurobiol. Aging 303 (1990). In 1991, Abraham C. et al., compared the cleavage pattern of the 68 Kd protease with known serine proteases. Abraham C. et al., 174 (2) Biochem. Biophys. Res. Comm. 790 (1991). Subsequently, the same researchers reported that the activity seen in the prior studies was actually the action of two independent proteases. One was identified as a calcium-dependent serine protease and the other a cysteine metalloprotease. Abraham C. et al., 15 (G) J. Cell Biochem. 115 (1991); Abraham C. et al., 57 J. Neurochem. 5109 (1991). No structure or characterization of these proteases was disclosed.

The present invention provides a new enzyme which is structurally different from those previously described and which will cleave APP to generate amyloidogenic fragments the size expected of a $Met_{596}$-$Asp_{597}$ cleavage. Thus, the new enzyme is very useful in furthering the characterization of Alzheimer's disease and Down's syndrome. Moreover, use of the invention may result in treatments for these or other related diseases.

DEFINITIONS

For purposes of clarity and as an aid in understanding the invention, as disclosed and claimed herein, the following items are defined below.

"Amyloidogenic fragment"—An APP fragment comprising the β/A4 peptide.

"Functional compound of SEQ ID NO:1"—A compound comprising SEQ ID NO:1 which is capable of cleaving APP.

"Kunitz-like domain"—A protease inhibitor similar to soybean trypsin inhibitor or a nucleic acid sequence encoding a protease inhibitor which is similar to the soybean trypsin inhibitor. For example, the Kunitz Protease Inhibitor (KPI) region of APP as described in Ponte p. et al., 331 Nature 525 (1988), or Tanzi R. E. et al., 331 Nature 528 (1988), or Kitaguchi N. et al., 331 Nature 530 (1988) is a Kunitz-like domain.

"pRc/Zyme"—A modified pRc/CMV eukaryotic expression vector (Invitrogen Catalog No. V750-20) which contains a human cytomegalovirus promoter and enhancer, a neomycin resistance gene, a beta-lactamase gene useful as an ampicillin resistance marker in E. coli, a NotI/SalI insert of 1451 base pairs which contains an entire Zyme coding region, and many other features as described in the 1991 Invitrogen Catalog, page 29.

"pSZyme"—A modified E.coli cloning vector pSPORT-1 (Gibco-BRL Catalog No. 5382SA) which contains an origin of replication from pUC vectors, the beta-lactamase gene which confers ampicillin resistance, a NotI/SalI insert of 1451 base pairs which contains an entire coding 1990 region of Zyme, and many other features as detailed in the Gibco/BRL Catalog and Reference Guide, page 355.

"Part of SEQ ID NO:1"—At least 6 consecutive amino acid residues or more of SEQ ID NO:1.

"mRNA"—RNA which has been transcribed either in vivo or in vitro, including, for example, RNA transcripts prepared in vitro via transcription of coding sequences of DNA by RNA polymerase.

"SEQ ID NO:1 and functional equivalents thereof"—SEQ ID NO:1 and conservative alterations of the amino acid sequence of SEQ ID NO:1, wherein the conservative alterations result in a compound which exhibits substantially the same biological, biochemical, chemical, physical and structural qualities of SEQ ID:1.

"SEQ ID NO:3"—The DNA sequence ATG GCT GGC GGC ATC ATA GTC AGG G.

"SEQ ID NO:4"—The DNA sequence AAC CGA ATC TTC AGG TCT TCC TGG GG.

"SEQ ID NO:5"—The DNA sequence TCG CTC TCT CCT GGG GAC ACA GA.

"SEQ ID NO:6"—The DNA sequence CCA GGT GCT ATT CCA TGT ATG TCA TAG.

"SEQ ID NO:7"—The DNA sequence TCT GTG TCC CCAGGA GAG AGC GA.

"SEQ ID NO:8"—The DNA sequence ATA GTG AAG CTG TCT TCT CAA T.

"Transfection"—any transfer of nucleic acid into a host cell, with or without integration of said nucleic acid into genome of said host cell.

"Zyme"—the amino acid sequence SEQ ID NO:1 and functional equivalents thereof.

"Zyme-related band configuration"—One of two band configurations chosen from two band configurations of a herein disclosed restriction fragment polymorphism. One pattern displays a 2400 base pair band, but no 2500 base pair band. The other pattern displays a 2500 band, but no 2400 base pair band.

SUMMARY OF THE INVENTION

The present invention provides amino acid compounds which comprise the amino acid sequence SEQ ID NO:1 and functional equivalents thereof. In particular, the amino acid compound which is SEQ ID NO:1 is preferred.

The invention also provides nucleic acid compounds which comprise a nucleic acid sequence which encodes the presently provided amino acid compounds or parts thereof. Particularly, nucleic acid compounds which are DNA are preferred. Most preferred is the DNA compound SEQ ID NO:2. However, also preferred are those nucleic acid compounds which are sense and antisense mRNA.

Also provided by the present invention are nucleic acid vectors comprising nucleic acids which encode SEQ ID NO:1 or functional equivalents thereof. The preferred nucleic acid vectors are those which are DNA. Most preferred are DNA vectors which comprise the DNA sequence which is SEQ ID NO:2. A most preferred DNA vector is pSZyme.

Moreover, DNA vectors of the present invention preferably comprise a promoter positioned to drive expression of said DNA sequence. Those vectors wherein said promoter functions in human embryonic kidney cells (293 cells), AV12 cells, yeast cells or *E. coli* cells are preferred. The DNA expression vector most preferred is plasmid pRc/Zyme.

Restriction fragments of the preferred vectors are also provided. Particularly, the 803 base pair BsrBI/Esp3I, the 815 base pair ECoNI/BfaI, and the 1451 base pair NotI/SalI restriction fragments of pSZyme are provided.

The present invention also provides probes and primers useful for molecular biology techniques. A compound which encodes all or part of SEQ ID NO:1 and which is at least 18 consecutive base pairs in length is provided. Preferably, the 18 base pair or more compound is DNA. Most preferred for this use are the DNA compounds which are SEQ ID NO:3 and SEQ ID NO:4.

Another embodiment of the present invention is a genomic clone of Zyme. The preferred genomic clone is the 4.0 kilobase HindIII fragment from a human chromosome 19 library which hybridizes to fragments of DNA which encode SEQ ID NO:1.

The present invention also provides an Alzheimer's disease diagnostic assay wherein donor human DNA is 1) digested with Taq I restriction enzyme, and 2) hybridized with labelled Zyme DNA to reveal a Zyme-related band configuration, and 3) compared to the similarly-digested and hybridized band configurations of those members of the donor's family who display or displayed the symptoms of Alzheimer's disease. The preferred Alzheimer's disease diagnostic assay utilizes a blood sample as the source of donor human DNA.

Host cells which harbor the nucleic acids provided by the present invention are also provided. A preferred host cell is an oocyte. A preferred oocyte is one which has been injected with sense mRNA or DNA compounds of the present invention. A more preferred oocyte is one which has been injected with sense mRNA or DNA compounds of the present invention in conjunction with DNA or sense mRNA which encodes APP.

Further, this invention provides cells in which the nucleic acid compounds of the invention my be transfected. Host cells include those which are transfected with a nucleic acid compound which encodes SEQ ID NO:1. Preferred cells include a host cell transfected with a DNA vector comprising SEQ ID NO:2.

The preferred transfected host cells which encode SEQ ID NO:1 are 293 cells, AV12 cells, yeast cells and *E. coli* cells. The most preferred transfected host cells are 293/pRc/Zyme, *E. coli*/pSZyme.

Also preferred is a host cell which has been co-transfected with a DNA vector which comprises SEQ ID NO:2 and a DNA vector which comprises the coding sequence of APP. 293 cells, AV12 cells, yeast cells and *E. coli* cells are the preferred co-transfected host cells.

Additionally, the invention provides a method for identifying DNA homologous to a probe of the present invention, which comprises combining test nucleic acid with the probe under hybridizing conditions and identifying those test nucleic acids which hybridize. The preferred probes for use in this method are SEQ ID NO:3 and SEQ ID NO:4.

Assays utilizing the compounds provided by the present invention are also provided. The assays provided determine whether a substance is a ligand for Zyme, said method comprising contacting Zyme with said substance, monitoring Zyme activity by physically detectable means, and identifying those substances which interact with or affect Zyme.

Preferred assays of the present invention include a cell culture assay, a high-performance liquid chromotography (HPLC) assay or a synthetic competition assay.

Preferred cell culture assays utilize oocytes, AV12, *E. coli*, yeast or 293 cells which co-express nucleic acids which encode Zyme and APP. Those co-expressing cell culture assays which are preferred include those which utilize 293/pRc/Zyme. A preferred assay utilizes yeast cells, and a DNA compound which encodes amino acids 587 to 606 of APP.

Most preferred oocyte assays co-express mRNA. Most preferred cell culture assays utilize Western blot analysis or radiolabelled APP as the physically detectable means.

A preferred HPLC assay is one wherein the substrate is full-length, eucaryotically-derived APP.

The most preferred synthetic competition assay is one wherein the substance competes with the Kunitz-like domain gene product for binding to Zyme. The most preferred Zyme/Kunitz domain competition assay is one wherein APP is labelled with radioisotope.

The invention also provides methods for constructing a host cell capable of expressing a nucleic acid compound which encodes a compound which comprises SEQ ID NO:1, said methods comprising transfecting a host cell with a DNA vector which comprises said nucleic acid compound. A preferred method utilizes 293, AV12, yeast or *E. coli* cells as the host cells. A more preferred method includes a DNA vector. A most preferred method further includes a DNA vector which comprises SEQ ID NO:2. Another preferred method comprises (a) a DNA vector which comprises SEQ ID NO:2 and (b) a DNA expression vector which encodes the APP coding sequence. A most preferred method utilizes the DNA vector DRC/Zyme.

Additionally, methods for expressing a nucleic acid sequence which encodes SEQ ID NO:1 or functional equivalents thereof in a transfected host cell are provided. These methods comprise culturing a transfected host cell provided by the present invention under conditions suitable for gene expression. A preferred method utilizes 293, AV12, yeast or *E. coli* cells as the host cell. A more preferred method utilizes a DNA vector. A most preferred method utilizes a DNA vector comprising all or part of SEQ ID NO:2. A most preferred method utilizes the DNA vector pRc/Zyme. Another preferred method utilizes oocytes. A most preferred method utilizes oocytes which have been injected with sense mRNA.

The present invention also provides a method for identifying or purifying Zyme, which comprises flooding test protein with anti-Zyme antibody, eliminating anti-Zyme antibody which fails to bind, and detecting anti-Zyme antibody which remains bound.

The following section provides a more detailed description of the present invention.

DETAILED DESCRIPTION OF THE INVENTION

The present invention provides an amino acid compound which comprises the amino acid sequence SEQ ID NO:1 and functional equivalents thereof. The preferred amino acid compound is SEQ ID NO:1, which is the following sequence of amino acids:

Other routes of production are well known. Expression in eucaryotic cells can be achieved via SEQ ID NO:2. For example, the amino acid compounds can be produced in

| Met 1 | Lys | Lys | Leu | Met 5 | Val | Val | Leu | Ser | Leu 10 | Ile | Ala | Ala | Ala | Trp 15 | Ala |
|---|---|---|---|---|---|---|---|---|---|---|---|---|---|---|---|
| Gly | Glu | Gln | Asn 20 | Lys | Leu | Val | His | Gly 25 | Gly | Pro | Cys | Asp | Lys 30 | Thr | Ser |
| His | Pro | Tyr 35 | Gln | Ala | Ala | Leu | Tyr 40 | Thr | Ser | Gly | His | Leu 45 | Leu | Cys | Gly |
| Gly | Val 50 | Leu | Ile | His | Pro | Leu 55 | Trp | Val | Leu | Thr | Ala 60 | Ala | His | Cys | Lys |
| Lys 65 | Pro | Asn | Leu | Gln | Val 70 | Phe | Leu | Gly | Lys | His 75 | Asn | Leu | Arg | Gln | Arg 80 |
| Glu | Ser | Ser | Gln | Glu 85 | Gln | Ser | Ser | Val | Val 90 | Arg | Ala | Val | Ile | His 95 | Pro |
| Asp | Tyr | Asp | Ala 100 | Ala | Ser | His | Asp | Gln 105 | Asp | Ile | Met | Leu | Leu 110 | Arg | Leu |
| Ala | Arg | Pro 115 | Ala | Lys | Leu | Ser | Glu 120 | Leu | Ile | Gln | Pro | Leu 125 | Pro | Leu | Glu |
| Arg | Asp 130 | Cys | Ser | Ala | Asn | Thr 135 | Thr | Ser | Cys | His | Ile 140 | Leu | Gly | Trp | Gly |
| Lys 145 | Thr | Ala | Asp | Gly | Asp 150 | Phe | Pro | Asp | Thr | Ile 155 | Gln | Cys | Ala | Tyr | Ile 160 |
| His | Leu | Val | Ser | Arg 165 | Glu | Glu | Cys | Glu | His 170 | Ala | Tyr | Pro | Gly | Gln 175 | Ile |
| Thr | Gln | Asn | Met 180 | Leu | Cys | Ala | Gly | Asp 185 | Glu | Lys | Tyr | Gly | Lys 190 | Asp | Ser |
| Cys | Gln | Gly 195 | Asp | Ser | Gly | Gly | Pro 200 | Leu | Val | Cys | Gly | Asp 205 | His | Leu | Arg |
| Gly | Leu 210 | Val | Ser | Trp | Gly | Asn 215 | Ile | Pro | Cys | Gly | Ser 220 | Lys | Glu | Lys | Pro |
| Gly 225 | Val | Tyr | Thr | Asn | Val 230 | Cys | Arg | Tyr | Thr | Asn 235 | Trp | Ile | Gln | Lys | Thr 240 |
| Ile | Gln | Ala | Lys. 244 | | | | | | | | | | | | |

Those in the art will recognize that some alterations of SEQ ID NO:1 will fail to change the function of the amino acid compound. For instance, some hydrophobic amino acids may be exchanged for other hydrophobic amino acids, amino acids with similar side chains may be interchanged, basic amino acids may be interchanged with other basic amino acids, acidic amino acids may be interchanged with other acidic amino acids, small amino acids may be interchanged with other small amino acids or various other conservative changes may be made. Those altered amino acid compounds which confer substantially the same function in substantially the same manner as the exemplified amino acid compound are also included in the present invention.

Artisans will also recognize that this protein can be synthesized by a number of different methods. All of the amino acid compounds of the invention can be made by chemical methods well known in the art, including solid phase peptide synthesis or recombinant methods. Both methods are described in U.S. Pat. No. 4,617,149. Recombinant methods are preferred if a high yield is desired. A general method for the construction of any desired DNA sequence is provided in Brown et al., 68 *Methods in Enzymology* 109 (1979).

eucaryotic cells using simian virus 40, cytomegalovirus, or mouse mammary tumor virus-derived expression vectors comprising DNA which encodes SEQ ID NO:1. As well known in the art, some viruses are also appropriate vectors. For example, the adenovirus, the vaccinia virus, the herpes virus, the baculovirus, and the rous sarcoma virus are useful. Such a method is described in U.S. Pat. No. 4,775,624. Several alternate methods of expression are described in J. Sambrook, E. F. Fritsch & T. Maniatis, *Molecular Cloning: A Laboratory Manual* 16.3–17.44 (1989).

Other embodiments of the present invention are nucleic acid compounds which comprise nucleic acid sequences which encode SEQ ID NO:1. As skilled artisans recognize, the amino acid compounds of the invention can be encoded by a multitude of different nucleic acid sequences because most of the amino acids are encoded by more than one nucleic acid triplet. Because these alternate nucleic acid sequences would encode the same amino acid sequences, the present invention further comprises these alternate nucleic acid sequences. Preferably, the nucleic acid compound is DNA, sense or antisense mRNA. A most preferred embodiment of a DNA compound which encodes Zyme has this sequence:

|  |  |  |  |  | ATGA | AGAAGCTGAT | 14 |
|---|---|---|---|---|---|---|---|
| GGTGGTGCTG | AGTCTGATTG | CTGCAGCCTG | GGCAGAGGAG | CAGAATAAGT | TGGTGCATGG | | 74 |
| CGGACCCTGC | GACAAGACAT | CTCACCCCTA | CCAAGCTGCC | CTCTACACCT | CGGGCCACTT | | 134 |
| GCTCTGTGGT | GGGGTCCTTA | TCCATCCACT | GTGGGTCCTC | ACAGCTGCCC | ACTGCAAAAA | | 194 |
| ACCGAATCTT | CAGGTCTTCC | TGGGGAAGCA | TAACCTTCGG | CAAAGGGAGA | GTTCCCAGGA | | 254 |
| GCAGAGTTCT | GTTGTCCGGG | CTGTGATCCA | CCCTGACTAT | GATGCCGCCA | GCCATGACCA | | 314 |
| GGACATCATG | CTGTTGCGCC | TGGCACGCCC | AGCCAAACTC | TCTGAACTCA | TCCAGCCCCT | | 374 |

-continued

| | | | | | | |
|---|---|---|---|---|---|---|
| TCCCCTGGAG | AGGGACTGCT | CAGCCAACAC | CACCAGCTGC | CACATCCTGG | GCTGGGGCAA | 434 |
| GACAGCAGAT | GGTGATTTCC | CTGACACCAT | CCAGTGTGCA | TACATCCACC | TGGTGTCCCG | 494 |
| TGAGGAGTGT | GAGCATGCCT | ACCCTGGCCA | GATCACCCAG | AACATGTTGT | GTGCTGGGGA | 554 |
| TGAGAAGTAC | GGGAAGGATT | CCTGCCAGGG | TGATTCTGGG | GGTCCGCTGG | TATGTGGAGA | 614 |
| CCACCTCCGA | GGCCTTGTGT | CATGGGGTAA | CATCCCCTGT | GGATCAAAGG | AGAAGCCAGG | 674 |
| AGTCTACACC | AACGTCTGCA | GATACACGAA | CTGGATCCAA | AAAACCATTC | AGGCCAAG | 732 |

This is the sequence identified as SEQ ID NO:2.

E. coli/pSZyme, which contains a cloning vector comprising SEQ ID NO:2, was deposited and made part of the stock culture collection of the Northern Regional Research Laboratories (NRRL), Agricultural Research Service, U.S. Department of Agriculture, Peoria, Ill., 61604 on Apr. 29, 1992, under the accession number NRRL B-18971. SEQ ID NO:2 can be isolated from the plasmid, for example, as a 1451 base pair NotI/SalI restriction fragment. Other fragments are useful in obtaining SEQ ID NO:2.

Additionally, the DNA sequences can be synthesized using automated DNA synthesizers, such as the ABS (Applied Biosystems, 850 Lincoln Centre Drive, Foster City, Calif. 94404) 380B DNA synthesizer. The DNA sequences can also be generated by the polymerase chain reaction (PCR) as described in U.S. Pat. No. 4,889,818.

Because artisans recognize that many vectors are available for expression and cloning, those expression and cloning vectors which comprise nucleic acids which encode SEQ ID NO:1 or a functional equivalent thereof or a part thereof are included in the present invention. Preferred nucleic acid vectors are those which are DNA. Most preferred DNA vectors comprise the DNA sequence SEQ ID NO:2. Plasmid pSZyme is a preferred DNA vector of the present invention.

Other preferred DNA vectors include those which comprise a promoter positioned to drive expression of SEQ ID NO:2. Preferred expression vectors include those which function in 293, AV12, yeast or E. coli cells. Most preferred is the expression vector pRc/Zyme.

Restriction fragments of these vectors are also provided. The preferred fragments are the 1451 base pair NotI/SalI restriction fragment, the 803 base pair BsrBI/Esp3I restriction fragment and the 815 base pair EcoNI/BfaI restriction fragment of pSZyme.

Plasmid pSZyme may be isolated from the deposited E. coli/pSZyme, using an ordinary cesium chloride DNA isolation procedure. Plasmid pSZyme is readily modified to construct expression vectors that produce Zyme in a variety of organisms, including, for example, E. coli, Sf9 (as host for baculovirus), Spodoptera and Saccharomycetes. For example, Serook et al., Molecular Cloning: A Laboratory Manual 16.30–16.67 (1989) explains these techniques.

The current literature contains techniques for constructing AV12 expression vectors and for transfecting AV12 host cells. For example, U.S. Pat. No. 4,992,373 explains these techniques.

The current literature also contains techniques for constructing 293 expression vectors and for transfecting 293 host cells. The construction protocols utilized for 293 can be followed to construct analogous vectors for other organisms, merely by substituting, if necessary, the appropriate regulatory elements using well known techniques. Promoters which my be used, for example, are the thymidine kinase promoter, the metallothionin promoter, the heat shock promoter, the mouse mammary tumor virus promoter or various other vital and immunoglobulin promoters.

The DNA compounds of the present invention also include primers and probes. Nucleic acid compounds of at least 18 consecutive base pairs which encode SEQ ID NO:1 or a part thereof are included in the present invention. Probes or primers which are DNA are preferred. Most preferred probes or primers are: SEQ ID NO:3 and SEQ ID NO:4. Those in the art will recognize the techniques associated with probes and primers as well known.

For example, all or part of SEQ ID NO:3 or SEQ ID NO:4 may be used to hybridize to the coding sequence. Then, through PCR amplification, the full length sequence may be generated. The full length sequence can be subsequently subcloned into any vector of choice.

Alternatively, SEQ ID NO:3 or SEQ ID NO:4 may be radioactively labeled at the 5' end in order to screen cDNA libraries by conventional means. Furthermore, any piece of Zyme-encoding DNA which has been bound to a filter may be flooded with total mRNA transcripts, in order to reverse-transcribe the mRNA transcripts which bind.

Primers and probes may be obtained by means well known in the art. For example, once pSZyme is isolated, restriction enzymes and subsequent gel separation may be used to isolate the fragment of choice.

Another embodiment of the present invention is a genomic clone of Zyme. The preferred genomic clone is the 4.0 kilobase HindIII fragment from a human chromosome 19 library which hybridizes to fragments of DNA which encode SEQ ID NO:1. This can be obtained via hybridization with SEQ ID NO:2, or parts thereof. For example, SEQ ID NO:3 and SEQ ID NO:4 may be radioactively labelled and used to probe a chromosome 19 library, in order to then identify and isolate the corresponding gaenomic DNA.

The present invention also provides an Alzheimer's disease diagnostic assay wherein donor human DNA is 1) digested with Taq I restriction enzyme, 2) hybridized with labelled Zyme DNA to reveal a Zyme-related band configuration, and 3) compared to the similarly-digested and hybridized band configurations of those members of the donor's family who display or displayed the symptoms of Alzheimer's disease. The preferred Alzheimer's disease diagnostic assay utilizes a blood sample as the source of donor human DNA.

Since the genomic DNA is provided in the present invention and a Zyme-related restriction fragment length polymorphism is identified by the disclosure of this invention, the remainder of this procedure may be accomplished according to methods known in the art. For example, U.S. Pat. No. 4,666,828, describes these procedures. Moreover, Lewin B., Genes 78 (1987) reviews restriction fragment length polymorphism techniques and theory.

Host cells which harbor the nucleic acids provided by the present invention are also provided. A preferred host cell is an oocyte. A preferred oocyte is one which has been injected with sense mRNA or DNA compounds of the present invention. A still more preferred oocyte is one which has been injected with sense mRNA or DNA compounds of the present invention in conjunction with DNA or mRNA which encodes APP. Most preferred oocytes of the present invention are those which have been injected with sense mRNA.

Other preferred host cells are those which have been transfected with a vector which comprises SEQ ID NO:2.

Preferred SEQ ID NO:2-transfected host cells include include 293, AV12, yeast and *E. coli* cells. Most preferred 293 and *E. coli* host cells are 293/pRc/Zyme, *E. coli*/pSZyme.

Also preferred is a host cell which has been co-transfected with a DNA vector which comprises SEQ ID NO:2 and a DNA vector which comprises the coding sequence of APP. 293 cells, AV12 cells, yeast cells and *E. coli* cells are especially useful co-transfected host cells.

An oocyte host cell can be constructed according to the procedure described in Lübbert, et al. 84 *Proc. Nat. Acad. Sci.* 4332 (1987). DNA or RNA which encodes APP (both the 695 and 751 amino acid forms) may be obtained as described in Selkoe et al., 85 *Proc. Nat. Acad. Sci.* 7341 (1988). Other host cell transfection is well known in the art. Co-transfection of cells may be accomplished according to Gorman et al., 2 *Mol. Cell Biol.* 1044 (1982).

Therefore, the present invention also provides a method for constructing a host cell capable of expressing SEQ ID NO:1, said method comprising transfecting a host cell with a DNA vector that comprises a DNA sequence which encodes SEQ ID NO:1. A preferred method utilizes 293 cells as host cells. 293 cells may be obtained from the ATCC under the accession number ATCC CRL 1573. Another preferred method utilizes AV12 cells as host cells. AV12 cells may be obtained from the ATCC under the accession number ATCC CRL 9595. Another preferred method utilizes yeast cells or *E. coli* as the host cells.

The preferred method utilizes an expression vector which comprises SEQ ID NO:2 in 293 cells. Especially preferred for this purpose is pRc/Zyme.

Another preferred method comprises (a) a DNA vector which comprises SEQ ID NO:2 and (b) a DNA expression vector which encodes the APP coding sequence. A most preferred method utilizes the DNA vector pRc/Zyme. Transfected host cells may be cultured under conditions well known to skilled artisans such that SEQ ID NO:1 is expressed, thus producing Zyme in the transfected host cell.

Also provided by the present invention is a method for expressing a nucleic acid which encodes SEQ ID NO:1 in a transfected host cell, said method comprising culturing said transfected host cell under conditions suitable for nucleic acid expression. The preferred method utilizes 293, AV12, yeast or *E. coli* cells. Another preferred method utilizes DNA. An even more preferred method utilizes DNA which is SEQ ID NO:2. The most preferred method utilizes 293 cells as host cells for pRc/Zyme. Another preferred method utilizes oocytes as host cells. The preferred method in oocytes utilizes sense mRNA. Expression in host cells may be accomplished according to the procedures outlined in Sambrook, et al., *Molecular Cloning: A Laboratory Manual* 16–17 (1989).

Additionally, the invention provides a method for identifying DNA homologous to a probe of the present invention, which comprises combining the test nucleic acid with the probe under hybridizing conditions and identifying those test nucleic acids which hybridize. The preferred method utilizes SEQ ID NO:3 and SEQ ID NO:4. Hybridization techniques are well known in the art. For example, Sambrook, et al., *Molecular Cloning: A Laboratory Manual* 11 (1989) describes such procedures.

Additional assays provided by this invention determine whether a substance is a ligand for Zyme, said assay comprising contacting Zyme with said substance, monitoring Zyme activity by physically detectable means, and identifying those substances which interact with or affect Zyme.

Preferred assays include a cell culture assay, a high-performance liquid chromotography (HPLC) assay and a synthetic competition assay.

Preferred cell culture assays utilize oocytes, yeast, AV12, *E. coli* or 293 cells which co-express nucleic acids which encode Zyme and APP. A preferred yeast assay utilizes a DNA compound which encodes amino acids 587 to 606 of APP. The yeast assay my be accomplished according to Smith and Kohorn, 88 *Proc. Nat. Acad. Sci.* 5159 (1991), with substitutions of Zyme-encoding DNA and APP-encoding DNA which comprises the $Met_{596}/Asp_{597}$ cleavage site codons.

Most preferred oocyte assays co-express mRNA. Especially useful physically detectable means are Western blot analysis or radioactively-labelled APP.

A preferred HPLC assay is one wherein the substrate is full-length, eukaryotically-derived APP.

The most preferred synthetic competition assay is one wherein the substance competes with a Kunitz-like domain for binding to Zyme. The most preferred Zyme/Kunitz-like domain competition assay is one wherein APP is labelled with radioisotope.

The cell culture assays may be accomplished according to the procedures detailed by Ausubel F. e al., Current Protocols in Molecular Biology, 9.1–9.5 (1989). The HPLC assay may be accomplished according to the procedures detailed in Hirs and Timasheff, eds. 91 Methods in Enzymology Sections V and VI (1983). The Zyme/Kunitz-like domain binding or competition assay may be accomplished according to the procedures detailed by Bennet J. and Yamamura H., *Neurotransmitter Receptor Binding*, Chapter 3 (1985).

The present invention also provides a method for identifying or purifying Zyme, which comprises flooding test protein with anti-Zyme antibody, eliminating anti-Zyme antibody which fails to bind, and detecting the anti-Zyme antibody which remains bound. Antibody imaging techniques are known in the art.

The following are examples of the present invention:

EXAMPLE 1

Production of Zyme in 293 Cells

A lyophil of *E. coli* pSZyme can be obtained from the Northern Regional Research Laboratories, Peoria, Ill. 61604 under the accession number NRRL B-18971 and used directly as the culture in the process described below.

Plasmid pSZyme was isolated from a culture of *E. coli*/pSZyme by CsCl purification. Plasmid pSZyme was then digested with SalI and NotI. The resulting fragment was linear. Ligase was used to ligate a SalI-NotI fragment and a SalI-HindIII linker into a previously linearized pRc plasmid. (Invitrogen, catalog #V750-20)

Competent *E. coli* cells were then transfected with the newly-created pRc/Zyme vector which contained SEQ ID NO:2 and selected for those cells which contained the ampicillin resistance gene by growing on ampicillin-containing medium.

After transfection of the pRc/Zyme vector into *E. coli*, a subsequent plasmid preparation was made in order to isolate the pRc/Zyme vector. In order to transfect 293 cells with the pRc/Zyme vector, the procedure according to Chen C. and OkayamaH., Molecular and Cellular Biology, Vol. 7, No. 8 2745 (1987) was used. These cells were used in the cell culture assay as described in Example 2.

Selection on G418 (Gibco) was included in this step to produce stable transformants in 293 cells. The colonies which grew in the presence of G418 were then used as a source of Zyme.

EXAMPLE 2

Cell Culture Assay

Human embryonic kidney cells (293 cells) were co-transfected with pRcZyme and an APP-encoding vector.

On one occasion, a vector encoding the 695 amino acid APP (which lacks a Kunitz-like domain) was cotransfected with pRcZyme. On another occasion, a vector encoding the 751 amino acid APP (with the Kunitz-like domin) was cotransfected with pRcZyme.

Transfection was achieved using Stratagene Catalog No. 200285—Calcium Phosphate Transfection System. However, transfection protocols as described by Maniatis 16.3–16.53 will also prove effective. Amyloidogenic fragments were detected when the 695 amino acid (without KPI) APP coding sequence was used, via Western Blot analysis as described by Maniatis 18.60 using antisera to the carboxy-terminal amino acids of the APP protein. Anti BX6, as decribed in Oltersdorf, T et al., J. Biol Chem, 265:4492–4497) was used in this procedure. Amyloidogenic fragments were not detected when the 751 amino acid (with KPI) APP was used.

EXAMPLE 3

HPLC Assay

Full-length APP is produced in cells which have been infected with APP-encoding baculovirus. This procedure is accomplished according to Knops J. et al., 266 (11) J. Biol. Chem. 7285 (1991). APP is then incubated in the presence of active Zyme and test compound. APP fragments are subsequently separated by high performance liquid chromotography. Each pooled fragment is then microsequenced according to Hirs and Timasheff, eds, 91 Methods in Enzymology Sections V and VI, (1983). The quantity of amyloidogenic fragments (those which terminate at either $Met_{596}$ or $ASP_{597}$) generated are compared to the quantity generated in the absence of test compouhd to determine the ability of the test compound to affect Zyme.

EXAMPLE 4

Zyme/Kunitz-like Domain Competition Assay

A peptide representing the KPI domain of APP is synthesized and labelled with isotope $I^{125}$. Competition binding assays are then conducted according to Bennet J. P. and Yamamura H., Neurotransmitter Receptor Binding 61 (1985). Zyme is then bound to plastic microtitre wells as in the traditional ELISA assay, which is detailed in Ausubel F., 2 Current Protocols in Molecular Biology 11.1–11.3 (1989). Radiolabelled KPI domain and unlabelled competitor compound is subsequently added to the wells of the 96-well microtitre plate. The wells are then washed. The remaining isotope is recorded in order to calculate the relative affinity of the unlabelled competitor compound to Zyme.

EXAMPLE 5

Isolating the Genomic Clone

A human chromosome 19 genomic library was purchased from American Type Culture Collection (ATCC) (Cat. no. 57711) with an E. coli K802 Rec A-host strain (Cat. no. 47026). The titre was $6.5-7.0\times10^4$ pfu/µL. A genomic clone was isolated by conventional screening of phage libraries (Sambrook et al., Molecular Cloning: A Laboratory Manual 2.6–2.114, 1989).

A radiolabelled cDNA probe was synthesized utilizing the polymerase chain reaction (Schowalter and Sommer 177 Anal. Biochem. 90–94, 1989) by specifically annealing SEQ ID NO:5 and SEQ ID NO:6 primers to an EcoRI/NotI purified (Bio-Rad Cat. no. 732-6010) pRc/Zyme DNA fragment.

Hybridization and washing was carried out at 65° C. as described in the Zeta-Probe Blotting Membrane instruction manual (Bio-Rad Cat. no. 164-0153). Positive plaques were stored in SM buffer containing 2–3 drops of chloroform. One of these plaques (711-4) was plaque purified. Lambda bacteriophage DNA from 711-4 was isolated using the reagents and protocols provided in the lambda maxi kit (Qiagen Cat. no. 12523).

Purified lambda phage Zyme DNA was digested with HindIII and electrophoresed on a 1% agarose/TBE (0.1M Tris-Cl pH 8.3, 0.1M Borate, 1 mM EDTA) gel. Separated DNA was then transferred onto a Zeta-Probe blotting membrane (0.5×TBE running buffer, constant 80 volts for 1 hour) as described in section 2.5 of the Zeta-Probe instruction manual using non-denaturing conditions, then denatured (0.4M NaOH for 10 minutes) as described in section 2.8 of the Zeta-Probe instruction manual.

A radiolabelled probe encompassing the BamHI/XbaI fragment of pRc/Zyme was used with a random primed DNA labelling kit (Boehringer Mannheim Cat. no. 1004760) to determine if the 3' coding sequence was found in our clone. Hybridization and washing to the above Zeta-Probe membrane was performed as previously described and autoradiography revealed homology to the 3' region of Zyme.

To confirm that phage 711-4 contained the 5' Zyme coding region, the polymerase chain reaction using SEQ ID NO:7 and SEQ ID NO:8 was again utilized to specifically amplify a 470 base pair band from tertiary plaque purified chromosome 19 Zyme phage DNA according to Kainz et al., 202 Anal. Biochem. 46 (1992). This DNA fragment was double gene cleaned according to an addendum to Gene Clean kit instructions (BIO 101 Cat. no. 3106), then subcloned into the pUC 19 plasmid. Nucleotides 1 to 33 of the 5' Zyme cDNA coding region and an additional 272 nucleotides upstream of the 5' Zyme coding region were confirmed using the kit and protocols provided from the Sequenase version 2.0 sequencing kit (USB Cat. no. 70770).

---

We claim:

1. A purified protease which comprises the amino acid sequence SEQ ID NO:1, or a functional equivalent thereof produced by conservative amino acid alterations which result in a protease which exhibits the same biological, biochemical, chemical, physical and structural properties of the protease of SEQ ID NO:1.

2. The purified protease of claim 1 which is SEQ ID NO:1.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 244 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Met Lys Lys Leu Met Val Val Leu Ser Leu Ile Ala Ala Ala Trp Ala
1               5                   10                  15

Glu Glu Gln Asn Lys Leu Val His Gly Gly Pro Cys Asp Lys Thr Ser
            20                  25                  30

His Pro Tyr Gln Ala Ala Leu Tyr Thr Ser Gly His Leu Leu Cys Gly
        35                  40                  45

Gly Val Leu Ile His Pro Leu Trp Val Leu Thr Ala Ala His Cys Lys
    50                  55                  60

Lys Pro Asn Leu Gln Val Phe Leu Gly Lys His Asn Leu Arg Gln Arg
65                  70                  75                  80

Glu Ser Ser Gln Glu Gln Ser Ser Val Val Arg Ala Val Ile His Pro
                85                  90                  95

Asp Tyr Asp Ala Ala Ser His Asp Gln Asp Ile Met Leu Leu Arg Leu
            100                 105                 110

Ala Arg Pro Ala Lys Leu Ser Glu Leu Ile Gln Pro Leu Pro Leu Glu
            115                 120                 125

Arg Asp Cys Ser Ala Asn Thr Thr Ser Cys His Ile Leu Gly Trp Gly
    130                 135                 140

Lys Thr Ala Asp Gly Asp Phe Pro Asp Thr Ile Gln Cys Ala Tyr Ile
145                 150                 155                 160

His Leu Val Ser Arg Glu Glu Cys Glu His Ala Tyr Pro Gly Gln Ile
                165                 170                 175

Thr Gln Asn Met Leu Cys Ala Gly Asp Glu Lys Tyr Gly Lys Asp Ser
            180                 185                 190

Cys Gln Gly Asp Ser Gly Gly Pro Leu Val Cys Gly Asp His Leu Arg
        195                 200                 205

Gly Leu Val Ser Trp Gly Asn Ile Pro Cys Gly Ser Lys Glu Lys Pro
    210                 215                 220

Gly Val Tyr Thr Asn Val Cys Arg Tyr Thr Asn Trp Ile Gln Lys Thr
225                 230                 235                 240

Ile Gln Ala Lys
```

( 2 ) INFORMATION FOR SEQ ID NO:2:

( i ) SEQUENCE CHARACTERISTICS:
( A ) LENGTH: 732 base pairs
( B ) TYPE: nucleic acid
( C ) STRANDEDNESS: both
( D ) TOPOLOGY: linear ( i i ) MOLECULE TYPE: cDNA ( x i ) SEQUENCE DESCRIPTION: SEQ ID NO:2:

```
ATGAAGAAGC TGATGGTGGT GCTGAGTCTG ATTGCTGCAG CCTGGGCAGA GGAGCAGAAT     60
AAGTTGGTGC ATGGCGGACC CTGCGACAAG ACATCTCACC CCTACCAAGC TGCCCTCTAC    120
ACCTCGGGCC ACTTGCTCTG TGGTGGGGTC CTTATCCATC CACTGTGGGT CCTCACAGCT    180
GCCCACTGCA AAAAACCGAA TCTTCAGGTC TTCCTGGGGA AGCATAACCT TCGGCAAAGG    240
GAGAGTTCCC AGGAGCAGAG TTCTGTTGTC CGGGCTGTGA TCCACCCTGA CTATGATGCC    300
GCCAGCCATG ACCAGGACAT CATGCTGTTG CGCCTGGCAC GCCCAGCCAA ACTCTCTGAA    360
CTCATCCAGC CCCTTCCCCT GGAGAGGGAC TGCTCAGCCA ACACCACCAG CTGCCACATC    420
CTGGGCTGGG GCAAGACAGC AGATGGTGAT TTCCCTGACA CCATCCAGTG TGCATACATC    480
CACCTGGTGT CCCGTGAGGA GTGTGAGCAT GCCTACCCTG GCCAGATCAC CCAGAACATG    540
```

| TTGTGTGCTG | GGGATGAGAA | GTACGGGAAG | GATTCCTGCC | AGGGTGATTC | TGGGGGTCCG | 600 |
| CTGGTATGTG | GAGACCACCT | CCGAGGCCTT | GTGTCATGGG | GTAACATCCC | CTGTGGATCA | 660 |
| AAGGAGAAGC | CAGGAGTCTA | CACCAACGTC | TGCAGATACA | CGAACTGGAT | CCAAAAAACC | 720 |
| ATTCAGGCCA | AG | | | | | 732 |

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

| ATGGCTGGCG | GCATCATAGT | CAGGG | 25 |

( 2 ) INFORMATION FOR SEQ ID NO:4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

| AACCGAATCT | TCAGGTCTTC | CTGGGG | 26 |

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

| TCGCTCTCTC | CTGGGACAC | AGA | 23 |

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

| CCAGGTGCTA | TTCCATGTAT | GTCATAG | 27 |

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

TCTGTGTCCC CAGGAGAGAG CGA  23

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

ATAGTGAAGC TGTCTTCTCA AT  22